United States Patent [19]

Gardner

[11] Patent Number: 4,782,144

[45] Date of Patent: Nov. 1, 1988

[54] 1-CARBA(DETHIA)-3-HYDROXY-3-CEPHEM ESTER CRYSTALLINE AND CRYSTALLINE SOLVATE THEREOF

[75] Inventor: John P. Gardner, Indianapolis, Ind.

[73] Assignee: Eli Lilly and Company, Indianapolis, Ind.

[21] Appl. No.: 95,721

[22] Filed: Sep. 14, 1987

[51] Int. Cl.$^4$ ............................................. C07D 471/04
[52] U.S. Cl. ................................................... 540/205
[58] Field of Search ......................................... 540/205

[56] References Cited

U.S. PATENT DOCUMENTS 4,237,279  12/1980  Fisher .................................... 544/16
4,665,171  5/1987  Evans et al. ......................... 540/364

OTHER PUBLICATIONS

Hatanaka, M., et al., *Tetrahedron Letters*, vol. 24, No. 44, pp. 4837–4838, 1983.
Evans, D. A. et al., *Tetrahedron Letters*, vol. 26, No. 32, pp. 3783–3786, 1985.
Evans, D. A. et al., *Tetrahedron Letters*, vol. 26, No. 32, pp. 3787–3790, 1985.

*Primary Examiner*—Mark L. Berch
*Attorney, Agent, or Firm*—William B. Scanlon; Leroy Whitaker

[57] ABSTRACT

Crystalline p-nitrobenzyl 7$\beta$-phenoxyacetylamino-3-hydroxy-1-carba(dethia)-3-cephem-4-carboxylate and the crystalline mono-acetic acid solvate thereof are provided by mixing a carboxylic acid or a sulfonic acid with a solution of the 3-hydroxy ester in DMF or DMAC. Acetic acid provides the crystalline acetic acid solvate while other acids provide crystalline non-solvated 3-hydroxy ester. The crystalline forms are useful purified intermediates to antibiotics.

7 Claims, 2 Drawing Sheets

1-CARBA(DETHIA)-3-HYDROXY-3-CEPHEM ESTER CRYSTALLINE AND CRYSTALLINE SOLVATE THEREOF

BACKGROUND OF THE INVENTION

This invention relates to crystalline intermediates useful for preparing antibiotic compounds and to a process for obtaining the crystalline intermediates. In particular, it relates to 4-nitrobenzyl 7β-phenoxyacetylamino-3-hydroxy-1-carba(dethia)ceph-3-em-4-carboxylate in crystalline form and to the crystalline acetic acid solvate thereof.

The preparation of 1-carbacephalosporin antibiotics generally entails numerous steps, particularly if the synthesis is asymmetric. Examples of such preparative multi-step methods is the asymmetric method described by Evans, et al., *Tetrahedron Letters*, Vol. 26, pp. 3787–3790, 1985, and the method described by Hatanaka, et al., *Tetrahedron Letters*, Vol. 24, pp. 4837–4839, 1983. In such syntheses the intermediates in the individual steps are desirably obtained in highly purified form for use in succeeding steps. The crystallinity of intermediates reflects their purity and is highly desirable since unwanted side reactions involving impurities can be avoided in subsequent steps of the overall process.

SUMMARY

7β-Phenoxyacetylamino-3-hydroxy-1-carba(dethia)-3-cephem-4-carboxylic acid p-nitrobenzyl ester is provided in stable crystalline form by mixing a solution of the ester in dimethylformamide (DMF) or dimethylacetamide (DMAC) with a carboxylic acid, e.g., formic acid, or a sulfonic acid, e.g., p-toluenesulfonic acid. Dilution of the solution of the ester with acetic acid provides the crystalline acetic acid solvate. The latter is a useful form for isolating the ester from crude mixtures thereof obtained in multistep processes.

Both crystalline forms of the ester are useful in the preparation of 3-halo-1-carba(dethia)-3-cephem antibiotic compounds.

DETAILED DESCRIPTION

This invention provides a crystalline intermediate represented by the following structural formula 1.

Figure 2:
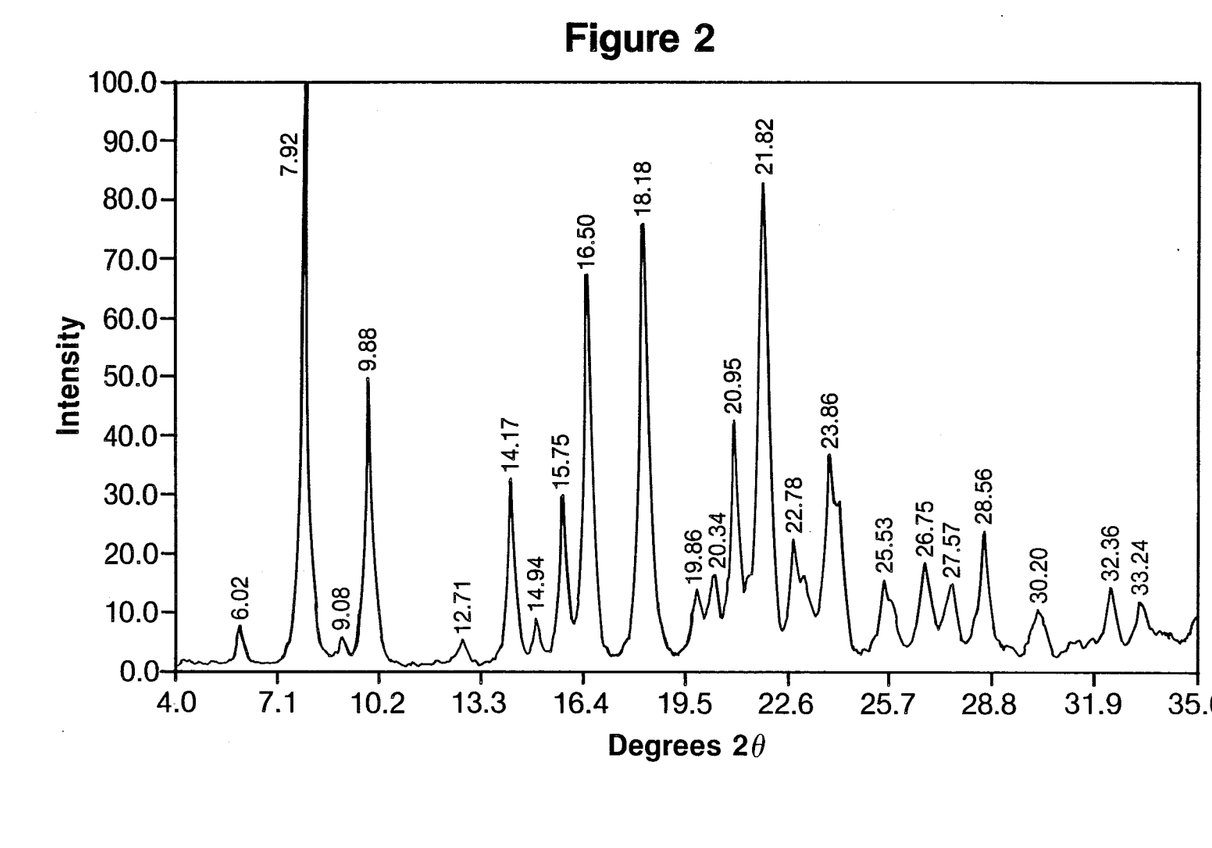
FIG. 2 is a computer-generated plot of the x-ray powder diffraction pattern of crystalline p-nitrobenzyl 7β-phenoxyacetylamino-3-hydroxy-1-carba(dethia)-3-cephem-4-carboxylate.

The crystalline form of 1 has a characteristic x-ray diffraction pattern. FIG. 2 of the drawings is a computer-generated plot of the diffraction pattern obtained with nickel-filtered copper radiation of λ1.54056 Å Kα wherein the angles of diffraction, 2-theta (2θ) and the intensities are plotted. Below are listed the interplanar spacings, dA, and the realtive intensities, $I/I_o$ calculated with the 2θ values.

| dA | $I/I_o$ |
| --- | --- |
| 14.66 | .04 |
| 11.15 | .82 |
| 9.73 | .02 |
| 8.94 | .42 |
| 6.96 | .03 |
| 6.25 | .27 |
| 5.92 | .04 |
| 5.62 | .24 |
| 5.37 | .61 |
| 4.88 | .95 |
| 4.47 | .12 |
| 4.36 | .14 |
| 4.24 | .41 |
| 4.07 | 1.00 |
| 3.90 | .25 |
| 3.73 | .48 |
| 3.49 | .17 |
| 3.33 | .16 |
| 3.23 | .13 |
| 3.12 | .22 |
| 2.96 | .11 |
| 2.76 | .10 |
| 2.69 | .09 |

The invention also provides the crystalline acetic acid solvate of 1 which is represented by the following formula 2.

Figure 1:
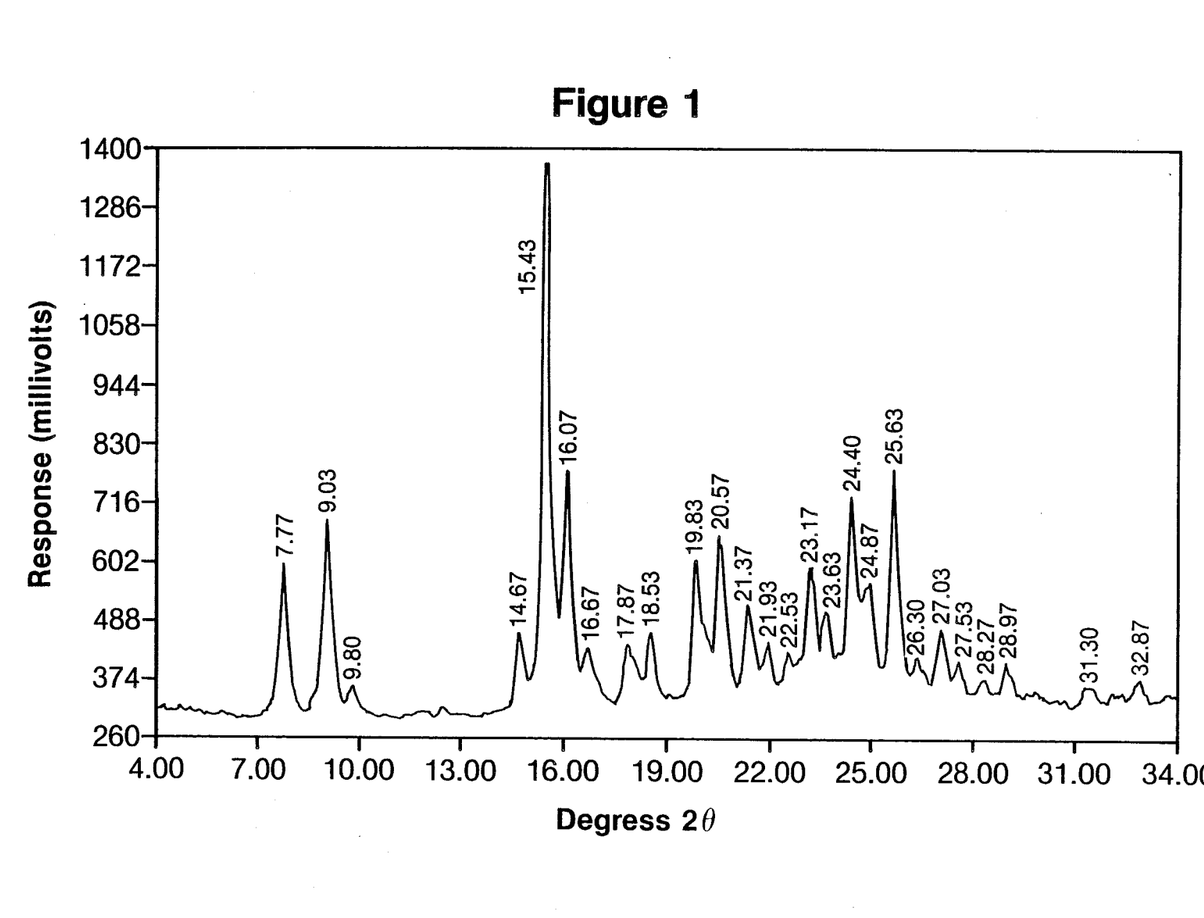
FIG. 1 is a computer-generated plot of the x-ray powder diffraction pattern of the mono-acetic acid solvate of the above-named 3-hydroxy-1-carba(dethia)-3-cephem ester.

The crystalline acetic acid solvate is obtained as white needles and exhibits the characteristic x-ray diffraction pattern shown by the computer-generated plot of FIG. 1. As with the crystalline non-solvated 3-hydroxy ester 1, the diffraction pattern was obtained using nickel-filtered copper x-radiation of $\lambda 1.54056$ Å $K\alpha_1$. The interplanar spacings and the relative intensities calculated as for FIG. 2 are shown below.

| dA | I/I$_O$ |
| --- | --- |
| 11.37 | .26 |
| 9.79 | .36 |
| 9.01 | .05 |
| 6.03 | .16 |
| 5.74 | 1.00 |
| 5.51 | .40 |
| 5.31 | .14 |
| 4.96 | .13 |
| 4.79 | .10 |
| 4.47 | .30 |
| 4.31 | .29 |
| 4.15 | .19 |
| 4.05 | .09 |
| 3.94 | .08 |
| 3.84 | .24 |
| 3.76 | .17 |
| 3.65 | .36 |
| 3.58 | .23 |
| 3.47 | .42 |
| 3.39 | .08 |
| 3.30 | .14 |
| 3.24 | .06 |
| 3.15 | .04 |
| 3.08 | .07 |
| 2.86 | .04 |
| 2.72 | .04 |

The crystalline acetic acid solvate 2 is stable under ordinary conditions of temperature and humidity. For example, it is dried at 45° C. without loss of crystallinity. The acetic acid solvate is useful for recovering the 3-hydroxy-1-carba-3-cephem ester from the reaction mixture in which it is formed, for example, as described herein by Example 2, or from reaction mixtures in which it is used as an intermediate and not all is converted. Alternatively, the solvate can be used to purify isolated crude ester to a crystalline form.

The crystalline acetic acid solvate 2 can be converted to the non-solvated crystalline ester 1 by first slurrying the solvate in a solvent mixture of methanol and acetonitrile, separating the crystalline material and slurrying the recovered crystals in methanol alone.

The 3-hydroxy ester crystalline form 1 and the crystalline acetic acid solvate 2 are both obtained in a process provided by this invention. According to the process, a solution of non-crystalline or impure ester 1 in dimethylformamide or dimethylacetamide is mixed with an acid selected from among a carboxylic acid represented by the formula RCOOH, wherein R is hydrogen, $C_1$–$C_8$ alkyl, $C_2$–$C_8$ alkenyl, substituted $C_1$–$C_8$ alkyl and substituted $C_2$–$C_8$ alkenyl substituted by halogen, carboxy, hydroxy or $C_1$–$C_4$ alkoxy; and a sulfonic acid represented by the formula $R_1SO_3H$, wherein $R_1$ is $C_1$–$C_4$ alkyl, phenyl or phenyl substituted by one or two of the same or different groups selected from among $C_1$–$C_4$ alkyl, $C_1$–$C_4$ alkoxy, halogen or hydroxy; and, when R of the carboxylic acid RCOOH is methyl, separating the crystalline precipitate of the mono-acetic acid solvate; and, when R of the carboxylic acid is other than methyl or the acid is a sulfonic acid, separating the crystalline precipitate of non-solvated 1.

Preferably, the crystallization process is carried out in DMF with 1 at a concentration of between about 50 mg/ml and about 300 mg/ml. Higher concentrations in the range are preferred.

The amount of acid mixed with the solution may be varied; however, an excess is preferably used. Preferably, for liquid acids a volume of acid corresponding to the volume of the enol solution is mixed. Solid acids may be mixed as such or as a solution in DMF or DMAC. Generally, about a 3 to 10 molar excess of the solid acid is employed.

The crystallization process can be carried out at room temperature or at somewhat colder temperature, e.g., between about 15° C. and 30° C. The DMF or DMAC is dried over molecular sieves prior to use in the process.

Examples of carboxylic acids RCOOH which can be used are formic acid, acetic acid, propionic acid, butyric acid and valeric acid, 2-ethylhexanoic acid, glutaric acid, malonic acid, succinic acid, adipic acid, hydroxyacetic acid, lactic acid, β-bromopropionic acid, 4-methoxybutyric acid, maleic acid, acrylic acid, crotonic acid and fumaric acid.

Examples of sulfonic acids $R_1SO_3H$ are methanesulfonic acid, ethanesulfonic acid, n-butanesulfonic acid, phenylsulfonic acid, p-toluenesulfonic acid, p-chlorobenzenesulfonic acid, 3,4-dichlorophenylsulfonic acid, 4-hydroxyphenylsulfonic acid and like sulfonic acids.

After crystallization is complete, the crystalline material can be separated from the solution of the acid by conventional means, e.g., filtration, decantation or centrifugation.

The crystalline 3-hydroxy ester 1 is preferably obtained in the process with DMF as the solvent and concentrated formic acid (98%). Glacial acetic acid with DMF as solvent is preferably used in the process to obtain the crystalline 2.

The crystalline forms of the 3-hydroxy ester provide purified forms of the ester following multistep preparations. These crystalline forms of the ester are useful in subsequent reactions leading to antibiotic compounds.

For example, the crystalline ester can be reacted with diazomethane in a suitable solvent to form the corresponding 3-methoxy ester. The latter can be deesterified, e.g., with zinc and acid, to form 7β-phenoxyacetylamino-3-methoxy-1-carba(dethia)-3-cephem-4-carboxylic acid which has antibacterial activity. Also, the 3-hydroxy ester may be converted to the 3-chloro ester and the latter deesterified to provide the corresponding 3-chloro-4-carboxylic acid antibiotic. Chlorination of the 3-hydroxy ester can be carried out as described by Evans et al., U.S. Pat. No. 4,673,737.

The 3-hydroxy-1-carba-3-cephem ester in non-crystalline, non-solvated form is obtained by asymmetric total synthesis as follows.

The chiral azetidinone-2 represented by the following formula A is obtained as described by Evans et al., *Tetrahedron Letters*, Vol. 26, No. 32, pp. 3783-3786, 1985, and U.S. Pat. No. 4,665,171 by reduction with lithium in ammonia and tetrahydrofuran at 31 78° C. of the chiral azetidinone-2 as shown below.

(1) Li—NH$_3$
(2) phenoxyacetyl chloride

A

The lithium-ammonia reduction removes both the N-benzyl group and the 4-phenyloxazolidone group at the 3-position. The resulting 3β-aminoazetidin-2-one is then acylated with phenoxyacetyl chloride or penoxyacetic acid anhydride to provide A.

Azetidinone A is subjected to ozonolysis to provide the 4-(2-carboxyethyl)azetidinone represented by formula B The 4-(2-carboxyethyl) group of B is subjected to homologation with the magnesium salt of the mono-(4-nitrobenzyl)ester of malonic acid to form the β-keto ester-substituted azetidinone represented by formula C The β-keto ester C is converted to the diazo keto ester by diazo transfer with tosyl azide and the diazo ester is reacted with rhodium tetra-acetate as described by Evans et al., *Tetrahedron Letters*, Vol. 26, No. 32, pp. 3787-3790, 1985, to provide the 1-carba-3-hydroxy ester represented by formula 1

Alternatively, the 1-carba-3-hydroxy ester can be obtained by the process described by Evans et al., U.S. Pat. No. 4,665,171, wherein a 3β-protected amino-4-[2-(5-methoxy-1,4-cyclohexadiene-1-yl)ethyl]azetidin-2-one is subjected to ozonolysis to form the β-keto ester, methyl 5-[3β-(amino-protected)azetidin-2-one-4-yl]-3-oxapentanoate. The β-keto methyl ester is converted to the benzyl ester via transesterification with titanium tetrabenzyloxide and the latter is converted via diazo transfer to the diazo keto ester. The rhodium catalyzed cyclization of diazo keto ester provides benzyl 3β-(amino-protected)-3-hydroxy-1-carba(1-dethia)-3-cephem-4-carboxylate. Removal of the amino-protecting group, e.g., the t-BOC group, affords the 3β-amino ester, which upon acylation with phenoxyacetyl chloride or phenoxyacetic acid anhydride provides the 3-hydroxy ester represented by formula 1 in non-crystalline form.

The following Examples are provided to further illustrate the invention but are not intended to be limiting thereof.

EXAMPLE 1

4-Nitrobenzyl 7β-phenoxyacetylamino-3-hydroxy-1-carba(1-dethia)-3-cephem-4-carboxylate acetic acid solvate One gram of 4-nitrobenzyl 7β-phenoxyacetylamino-3-hydroxy-1-carba(1-dethia)-3-cephem-4-carboxylic acid was dissolved in 2.4 ml of DMF, the solution was filtered and the filter pad was washed with 0.9 ml of DMF. To the filtrate were added 3.3 ml of glacial acetic acid and the solution was stirred at room temperature for 7.5 hours. The crystalline precipitate was filtered, washed twice with 2 ml of acetic acid and dried for two days in a vacuum oven at 45° C. There was obtained 0.8 g (70.8% yield) of the acetic acid solvate as white needles.

Percent elemental composition calculated for $C_{25}H_{25}N_3O_{10}$:
Theory: C, 56.93; H, 4.78; N. 7.97
Found: C, 56.83; H, 4.55; N. 8.07
Field Desorption Mass Spectrum: 467
IR Spectrum (chloroform): 1763, 1713, 1690, 1674, 1525, 1385, 1350 cm$^{-1}$.
UV Spectrum ($C_2H_5OH$): 275 nm (12,363) 269 nm (12,414)

EXAMPLE 2

Preparation of acetic acid solvate from reaction mixture

A solution of 136.5 g of 4-nitrobenzyl 5-[3β-(phenoxyacetylamino)azetidin-2-one-4-yl]-2-diazo-3-oxapentanoate and 1.09 g of rhodium tetra-acetate in 1700 ml of methylene chloride maintained under nitrogen was heated at the reflux temperature for 4.25 hours. The green mixture was allowed to cool with stirring for 1.25 hours and was then concentrated by evaporation to a brown solution weighing 601.7 g. The solution was treated with 300 ml of DMF and then concentrated again to a brown solution weighing 482.1 g. To the concentrate were added 300 ml of glacial acetic acid and the mixture was seeded with crystals of the 3-hydroxy solvate previously prepared. The mixture was stirred for about 3 minutes and set up with formation of a heavy precipitate. To the mixture 300 ml of water were added dropwise with stirring over 10 minutes. After stirring for 20 minutes, the mixture was filtered, the precipitate washed with acetic acid:water, 1:1 by volume, and then was dried at 40° C. in a vacuum oven for two days. There were obtained 94.6 g of 4-nitrobenzyl 3β-phenoxyacetylamino-3-hydroxy-1-carba(1-dethia)-3-cephem-4-carboxylate acetic acid solvate as off-white crystals.

Percent elemental composition calculated for $C_{25}H_{25}N_3O_{10}$:
Theory: C, 56.93; H, 4.78; N, 7.97
Found : C, 57.15; H, 4.88; N, 7.84
UV Spectrum ($C_2H_5OH$): λmax 275 nm (14,788) λmax 269 nm (14,878)
Field Desorption Mass Spectrum: 467

EXAMPLE 3

Crystalline p-nitrobenzyl 7β-phenoxyacetylamino-3-hydroxy-1-carba(dethia)-3-cephem-4-carboxylate Non-crystalline p-nitrobenzyl 7β-phenoxyacetylamino-3-hydroxy-1-carba(dethia)-3-cephem-4-carboxylate, 2.34 g was dissolved in 7.95 ml of DMF (dried on molecular sieves) to form a yellow solution. Formic acid (7.95 ml of 98%) was added with stirring and the solution was filtered and allowed to stand at room temperature. The crystalline enol ester was collected by filtration, washed with 5 ml of 1:1, DMF:formic acid and dried at 40° C. in a vacuum oven. There was obtained 0.47 g of the title compound as white needles.

I claim:
1. The compound of the formula in crystalline form having the following x-ray powder diffraction pattern:

| dA | $I/I_O$ |
|---|---|
| 14.66 | .04 |
| 11.15 | .82 |
| 9.73 | .02 |
| 8.94 | .42 |
| 6.96 | .03 |
| 6.25 | .27 |
| 5.92 | .04 |
| 5.62 | .24 |
| 5.37 | .61 |
| 4.88 | .95 |
| 4.47 | .12 |
| 4.36 | .14 |
| 4.24 | .41 |
| 4.07 | 1.00 |
| 3.90 | .25 |
| 3.73 | .48 |
| 3.49 | .17 |
| 3.33 | .16 |
| 3.23 | .13 |
| 3.12⁻ | .22 |
| 2.96 | .11 |
| 2.76 | .10 |
| 2.69 | .09 |

2. The acetic acid solvate of the formula in crystalline form having the following x-ray powder diffraction pattern:

| dA | $I/I_O$ |
|---|---|
| 11.37 | .26 |
| 9.79 | .36 |
| 9.01 | .05 |
| 6.03 | .16 |
| 5.74 | 1.00 |
| 5.51 | .40 |
| 5.31 | .14 |
| 4.96 | .13 |
| 4.79 | .10 |
| 4.47 | .30 |
| 4.31 | .29 |
| 4.15 | .19 |
| 4.05 | .09 |
| 3.94 | .08 |
| 3.84 | .24 |
| 3.76 | .17 |
| 3.65 | .36 |
| 3.58 | .23 |
| 3.47 | .42 |
| 3.39 | .08 |
| 3.30 | .14 |
| 3.24 | .06 |
| 3.15 | .04 |
| 3.08 | .07 |
| 2.86 | .04 |
| 2.72 | .04 |

3. The process for preparing in crystalline form p-nitrobenzyl 7β-phenoxyacetylamino-3-hydroxy-1-carba(dethia)-3-cephem-4-carboxylate or the crystalline mono-acetic acid solvate thereof which comprises mixing at a temperature between about 15° C. and about 30° C. a solution of said 3-hydroxy p-nitrobenzyl ester in dimethylformamide or dimethylacetamide with a carboxylic acid RCOOH or a sulfonic acid $R_1SO_3H$ wherein R is hydrogen, $C_1$–$C_8$ alkyl, substituted $C_1$–$C_8$ alkyl substituted by halogen, carboxy, hydroxy or $C_1$–$C_4$ alkoxy, $C_2$–$C_8$ alkenyl or $C_2$–$C_8$ alkenyl substituted by halogen, carboxy, hydroxy or $C_1$–$C_4$ alkoxy, and $R_1$ is $C_1$–$C_4$ alkyl, phenyl or phenyl substituted by one or two of the same or different groups selected from $C_1$–$C_4$ alkyl, $C_1$–$C_4$ alkoxy, halogen or hydroxy; and when R is methyl, separating the said crystalline acetic acid solvate or when R is other than methyl or $R_1SO_3H$ is mixed, separating the said non-solvated crystalline 3-hydroxy p-nitrobenzyl ester.

4. The process of claim 3 wherein the concentration of the 3-hydroxy ester in dimethylformamide or dimethylacetamide is between about 50 mg/ml and about 300 mg/ml.

5. The process of claim 4 wherein the solvent is dimethylformamide.

6. The process of claim 5 wherein acetic acid is mixed and the crystalline mono-acetic acid solvate is separated.

7. The process of claim 5 wherein formic acid is mixed and the crystalline 3-hydroxy ester is separated.

* * * * *

UNITED STATES PATENT AND TRADEMARK OFFICE
CERTIFICATE OF CORRECTION

PATENT NO. : 4,782,144

DATED : November 1, 1988

INVENTOR(S) : John P. Gardner

It is certified that error appears in the above—identified patent and that said Letters Patent is hereby corrected as shown below:

Column 2, that part of the structural formula reading

"  "

should read

—  — .

Column 3, that part of the structural formula reading

"  "

UNITED STATES PATENT AND TRADEMARK OFFICE
CERTIFICATE OF CORRECTION

PATENT NO. : 4,782,144

DATED : November 1, 1988

INVENTOR(S) : John P. Gardner

It is certified that error appears in the above—identified patent and that said Letters Patent is hereby corrected as shown below:

should read --  -- .

Column 3, line 14, "cyrstalline" should read -- crystalline --.

Column 5, that part of the structural formula reading

"  "

should read --  -- .

Column 6, lines 5-8, that part of the structural formula reading

"  "

UNITED STATES PATENT AND TRADEMARK OFFICE
CERTIFICATE OF CORRECTION

PATENT NO. : 4,782,144
DATED : November 1, 1988
INVENTOR(S) : John P. Gardner It is certified that error appears in the above—identified patent and that said Letters Patent is hereby corrected as shown below:

should read --  -- .

Column 6, line 23, "penoxya-" should read -- phenoxya- --; lines 31-34, that portion of the structural formula appearing as

"  "

should read --  -- .

Column 6, lines 53-55, that portion of the structural formula appearing as

"  "

UNITED STATES PATENT AND TRADEMARK OFFICE
CERTIFICATE OF CORRECTION

PATENT NO. : 4,782,144
DATED : November 1, 1988
INVENTOR(S) : John P. Gardner It is certified that error appears in the above—identified patent and that said Letters Patent is hereby corrected as shown below:

should read --  -- .

Column 6, line 65, "tetra-acetate" should read -- tetraacetate --.

Column 7, that portion of the structural formula appearing as "  "

should read --  -- .

Column 7, line 66, "tetra-acetate" should read -- tetraacetate --.

UNITED STATES PATENT AND TRADEMARK OFFICE
CERTIFICATE OF CORRECTION

PATENT NO. : 4,782,144

DATED : November 1, 1988

INVENTOR(S) : John P. Gardner

It is certified that error appears in the above-identified patent and that said Letters Patent is hereby corrected as shown below:

Column 9, lines 4-7, that portion of the structural formula reading

"  "

should read

--  --.

Column 9, lines 45-48, that portion of the structural formula reading

"  "

should read

--  --.

Signed and Sealed this

Eighth Day of August, 1989

Attest:

DONALD J. QUIGG

Attesting Officer

Commissioner of Patents and Trademarks